Figure 1:
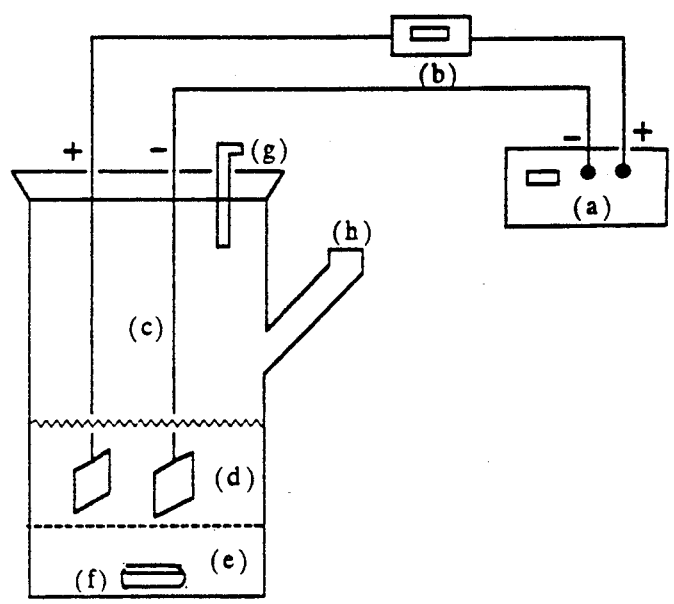

United States Patent [19]
Gao et al.

[11] Patent Number: 5,271,812
[45] Date of Patent: Dec. 21, 1993

[54] ELECTROCATALYTIC OXIDATION METHOD FOR THE PRODUCTION OF CYCLIC SULFATES AND SULFAMIDATES

[75] Inventors: Yun Gao, Framingham; Charles M Zepp, Berlin, both of Mass.

[73] Assignee: Sepracor, Inc., Marlborough, Mass.

[21] Appl. No.: 717,432

[22] Filed: Jun. 19, 1991

[51] Int. Cl.$^5$ .............................................. C25B 3/00
[52] U.S. Cl. .................................. 204/59 R; 204/78
[58] Field of Search .............................. 204/59 R, 78

[56] References Cited

PUBLICATIONS

Chemistry Letters, 1984, No. 7, pp. 1063-1066 by Torii et al. Jul., 1984.
Gau et al. B. J. Am. Chem. Soc., 1988, No. 110, pp. 7538-7541.
Torii et al., J. Org. Chem. 51: 155-161 (1986).
Gao, Y. and Sharpless K. B., J. Am. Chem. Soc. 110: 7538-7539 (1988).
Lohray et al., Tetrahedron Letters 30(2): 2626 (1989).
Kim, B. M. and Sharpless, K. B., Tetrahedron Letters 30: 655 (1989).
Baldwin et al., Tetrahedron: Asymmetry 1(12): 881-884 (1990).
Aiker et al., Tetrahedron: Asymmetry 1(12): 877-880 (1990).
Oi, R. and Sharpless K. B., Tetrahedron Letters 32(8): 999-1002 (1991).

Primary Examiner—John Niebling
Assistant Examiner—Patrick J. Igoe
Attorney, Agent, or Firm—Pennie & Edmonds

[57] ABSTRACT

The invention relates to a process for the production of cyclic sulfates and cyclic sulfamidates from the corresponding cyclic sulfite and cyclic sulfamidite substrate, respectively. The method involves the electrolysis of a solvent mixture containing active metal species, non-metal oxidant species and substrate.

20 Claims, 1 Drawing Sheet

ELECTROCATALYTIC OXIDATION METHOD FOR THE PRODUCTION OF CYCLIC SULFATES AND SULFAMIDATES

TABLE OF CONTENTS

1. Field of the Invention
2. Background of the Invention
3. Summary of the Invention
4. Brief Description of Figure
5. Detailed Description of the Invention
6. Examples
   6.1. General Experimental Conditions
   6.2 Electrolysis Apparatus
   6.3. Example 1 General Procedure for Electrocatalytic Oxidation of Cyclic Substrates
   6.4. Example-2
   6.5 Example-3
   6.6. Example-4
   6.7 Example-5
   6.8. Example-6
   6.9. Example-7
   6.10. Example-8
   6.11. Example-9
   6.12. Example-10
   6.13. Example-11
   6.14. Example-12
   6.15. Example-13

1. FIELD OF THE INVENTION

The present invention relates to the electrocatalytic oxidation of diol cyclic sulfites and cyclic sulfamidites of amino-alcohols to the corresponding cyclic sulfates and cyclic sulfamidates. The present method makes use of a catalytic amount of $RuCl_3$ or $RuO_2$ in a buffered aqueous NaCl solution along with a separate organic phase containing the substrate sulfite or sulfamidite. The oxidation process is thought to proceed with the oxidation of cyclic sulfite or sulfamidite with $RuO_4$ to the sulfate or sulfamidate, followed by regeneration of $RuO_4$ from Ru(III) or Ru(IV) species with the active chlorine species, $ClO^-$ or $Cl^+$, which, in turn, is produced at the anode from $Cl^-$.

2. BACKGROUND OF THE INVENTION

The oxidation of cyclic sulfites or sulfamidites to cyclic sulfates or sulfamidate is an important transformation because of the great utilities of cyclic sulfates and cyclic sulfamidates in organic synthesis. For synthetic applications of cyclic sulfates, please see: (a) Gao, Y. and Sharpless K. B. *J. Am. Chem. Soc.* 1988, 110, 7358. (b) Lohray, B. B.; Gao, Y.; Sharpless, K. B. *Tetrahedron Lett.* 1989, 30, 2623. (C) Kim, B. M.; Sharpless, K. B. Ibid., 1989, 30, 655. (d) Oi, R.; Sharpless, K. B. Ibid., 1991, 32, 999 and references cited therein. For synthetic applications of cyclic sulfamidates, please see: Baldwin, J. E.; Spivey, A. C.; Schofield, C. J. *Tetrahedron: Asymmetry*, 1990, 1, 881–884 and references cited therein. The oxidation reaction has been previously performed by using stoichiometric amounts of $RuO_4$. Recently, Gao, et al have developed a process using catalytic amounts of $RuCl_3$ and a stoichiometric amount of $NaIO_4$ or NaOCl as the reoxidant for the spent ruthenium species (Gao, Y. and Sharpless, K. B. *J. Am. Chem. Soc.* 1988, 110, 7538. However, this process involves of the use of expensive $NaIO_4$ or strong alkali NaOCl solution, thus limiting its utility to laboratory scale reactions.

Recently, a double mediatory system consisting of $RuO_4/RuO_2$ and $Cl^+/Cl^-$ redox couples has been used for the indirect electrooxidation of alcohols and aldehydes to the corresponding ketones or acids by Torri, et al. as reported in *J. Org. Chem.* 1986, 51, 155.

Thus, a catalytic scheme is needed for the electrooxidation of cyclic sulfites and sulfamidites to the corresponding cyclic sulfates and sulfamidates which is amendable to large scale production of product.

3. SUMMARY OF THE INVENTION

It has been discovered that cyclic sulfites and sulfamidites can be electrochemically oxidized to cyclic sulfates and sulfamidates with a metal species/non-metal reoxidant couple. In particular, the present invention involves a method of preparing a cyclic sulfate or sulfamidate compound of the formula (I) from the corresponding substrate of the formula (II),

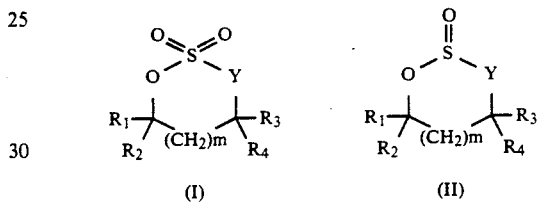

in which $R_1$, $R_2$, $R_3$ and $R_4$ may each, independently, be a hydrogen atom, a linear, branched or cyclic aliphatic alkyl group, which may optionally be substituted by one or more hetero atoms, a substituted or unsubstituted aromatic or heteroaromatic group, Y can be an oxygen or a group, $N-R_5$, in which $R_5$ is defined the same way as $R_1-R_4$ and m may be 0, 1 or 2, comprising:

(a) preparing an aqueous solvent medium that includes an effective amount of a metal species having a catalytically active state and an effective amount of a non-metal moiety that is capable of being oxidized electrochemically to an oxidant species;

(b) contacting said aqueous solvent medium with an organic solvent medium containing a substrate of the formula (II);

(c) applying a potential across a pair of electrodes that is in intimate contact with said aqueous solvent medium, such that said oxidant species is produced electrochemically and, through the action of said oxidant species, an amount of the catalytically active state of said metal species is maintained effective to mediate the production of the compound of the formula (I) from the oxidation of the substrate of the formula (II).

The reaction may be performed in an aqueous-organic two-phase system in an undivided cell under constant current using Pt metal foils as the electrodes. The aqueous phase may be a buffered NaCl solution and the organic may be an inert solvent such as $CCl_4$ or $CH_2Cl_2$ or an organic solvent mixture consisting of two or more solvents. The process is depicted in Scheme 1.

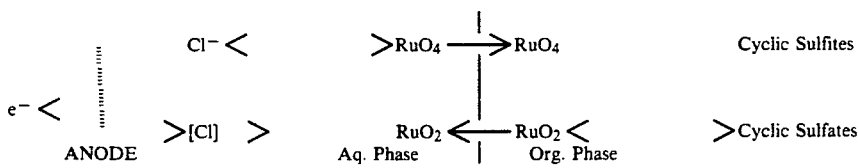

4. BRIEF DESCRIPTION OF FIGURE

FIG. 1 illustrates an electrolysis cell for constant current electrolysis: in which (a) power supply; (b) coulometer; (c) Pt foil electrodes; (d) aqueous phase; (e) organic phase; (f) stirring bar; (g) gas outlet; and (h) inlet feed.

5. DETAILED DESCRIPTION OF THE INVENTION

In a general embodiment of the present invention, a cyclic sulfite (II, Y=O) of a 1,n-dihydroxy compound in which n=2,3,4, or a cyclic sulfamidite (II, Y=N-$R_5$) of a 1,2-aminoalcohol is oxidized to the corresponding sulfate (I, Y=O) or sulfamidate (I, Y=N-$R_5$). In the course of this reaction, a new sulfur-oxygen double bond is formed on the central sulfur atom.

In one embodiment of the present invention, the electrocatalytic oxidation is performed in an undivided cell using platinum foils as the anode and cathode immersed in the upper aqueous phase of a two-phase system consisting of a saturated aqueous sodium chloride solution buffered at the desired pH and an organic phase of one or more inert solvents such as $CCl_4$, $CH_2Cl_2$, or mixtures thereof, including mixtures with acetonitrile. The catalyst may be any metal species having a catalytically active state for the conversion of the sulfite or sulfamidite, respectively. However, for economy, the catalyst is preferably $RuCl_3.3H_2O$ or $RuO_2$. The reaction is preferably performed at 20°-30° C. under a constant current of 20-40 mA/cm$^2$. The $RuCl_3$ or $RuO_2$ is first oxidized to $RuO_4$, and then the cyclic sulfite or cyclic sulfamidite is added to the reaction mixture. After all the cyclic sulfite or cyclic sulfamidite is consumed as indicated by a change in the color of the aqueous solution from a dark brown to yellow color, the reaction is quenched with isopropyl alcohol and the product is recovered by simple extraction and may be further purified by any means known in the art, such as recrystallization, distillation or chromatography. On a large scale production a circulating flow cell for constant current electrolysis is preferably used.

In a particular embodiments of the present invention, cyclic sulfites of 1,2-diols, such as L-diethyl tartrate, L-diisopropyl tartrate, 2,3-butanediol and 1,2-decanediol and the like and 1,3-diols, such as 1,3-propanediol and 2,4-pentanediol, and cyclic sulfamidites of 1,2-aminoalcohols, such as L-ephedrine cyclic sulfamidite are used as the starting materials. These substrate compounds can be readily made by reaction of thionyl chloride with the corresponding diols or aminoalchohols with or without the presence of a base, such as triethylamine, according to literature methods (See, for example, Breslow, D. S.; Skolnik, H. *Multi-sulfur and Sulfur and Oxygen Five- and Six-Membered Heterocycles*, Part One, Interscience Publishers (1966), chapter 1, and Deyrup, J. A.; Moyer, C. L. *J. Org. Chem.* 1969, 34, 175).

For small scale electrolyses, an undivided beaker cell, as shown in FIG. 1, is suitable. Larger vessels for large-scale production of product are easily envisioned and constructed according to methods well known in the art, such as the flow cell system described by Torri and co-workers. Platinum foils are immersed in the upper aqueous layer of the two-phase system and are used as the anode and cathode. In a preferred embodiment of the present invention, the aqueous phase is a sodium chloride solution, most preferably a saturated solution buffered between pH 4 to pH 9. The reaction is mostly performed at pH 7 and, in the case of the synthesis of a cyclic sulfamidate, at pH 8.5. The organic phase consists of one or two halogenated hydrocarbon solvents such as $CCl_4$, or $CH_2Cl_2$ or $CCl_4$-$CH_3CN$ or $CH_2Cl_2$-$CH_3CN$. volume ratio of aqueous to organic is usually 2 to 1 or 1 to 1, and preferably about 2 to 1.

The temperature is kept at 20°-30° C., preferably at ambient temperature of around 25° C. A water bath may be used if desired.

The reaction is performed at a constant current of 20-40 mA/cm$^2$, preferably at 20 mA/cm$^2$, using a power supply, and the amount of electricity used is monitored using a Coulometer. Generally, about 2-7 F/mole of electricity is used based on the cyclic sulfite or cyclic sulfamidite.

The preferred catalyst is $RuCl_3.3H_2O$ because it is the least expensive. However, any metal species having a catalytically active state may be employed. The amount of catalyst is usually 0.8-2 mole % of the cyclic sulfite or cyclic sulfamidite.

Generally, the reaction is performed, at ambient temperature, by addition of $RuCl_3.3H_2O$ to the electrolysis cell; a constant current of 20 mA/cm$^2$ is kept. After the $RuCl_3$ is transformed to $RuO_4$ (color of aqueous layer changes from dark brown to yellow), the cyclic sulfite or cyclic sulfamidite dissolved in small amount of $CCl_4$ or $CH_2Cl_2$ is added all at once with stirring and the solution turns to dark brown again. Alternatively, the substrate can be added progressively as the reaction proceeds. The reaction is continued at the same temperature and current with moderate stirring until all of the starting material is consumed as shown by the change in the color of the aqueous layer from dark brown to yellow. The current is stopped and the electrodes are removed and the reaction mixture is quenched with small amount of isopropyl alcohol to destroy the excess $RuO_4$. The reduced catalyst can be recovered by filtration and reused. The phases are then separated. The aqueous layer is extracted with $CH_2Cl_2$ and the combined organic phases are washed with brine and dried. The product is recovered by removal of solvent in vacuo and is usually very pure but can be further purified by chromatography on silica gel or distillation or recrystallization, if the product is a solid. The overall yield of the reaction is usually more than 80%.

In order to more fully illustrate the nature of the invention and the manner of practicing the same, the following examples, which are to be construed as merely illustrative, and not limitative of the balance of the disclosure in any way whatsoever, are presented.

6 EXAMPLES

6.1. General Experimental Conditions

All reagents are obtained from commercial sources and used without further purification unless otherwise stated. The cyclic sulfites are prepared from reaction of thionyl chloride and the corresponding diols in $CH_2Cl_2$ without or in the presence of $Et_3N$ according to literature procedures. The cyclic sulfamidites are prepared from reaction of thionyl chloride and the corresponding 1,2-aminoalchohols in the presence of $Et_3N$ in $CH_2Cl_2$ or EtOAc according to literature methods.

Analytical thin-layer chromatography (TLC) is performed on glass silica gel plates (0.25 mm thick E. Merck silica gel eluting with 15% ethyl acetate in hexane.

All proton NMR spectra are run on a Varian EM 360 60 MHz spectrometer using $CDCl_3$ as the solvent and tetramethylsilane as an internal standard. Infrared spectra are taken on a Nicolet 5DXC FT-IR spectrometer. Optical rotations are obtained on a Perkin-Elmer 243 polarimeter.

6.2. Electrolysis Apparatus

Electrolyses are usually carried out in a 200 mL undivided glass beaker cell (5 cm diameter and 16 cm height) fitted with an inlet side arm, a gas outlet, a stirring bar and two platinum foil electrodes (5 $cm^2$ in size) placed parallel to each other 2.5 cm apart (FIG. 1). The cell is immersed in a water bath maintained in a range of 20°–30° C. The electrodes are connected to a constant current power supply and a coulometer. During the electrolysis, the polarity of the electrodes are switched occasionally to prevent electrode fouling.

6.3. Example-1 General Procedure for Electrocatalytic Oxidation of Cyclic Substrates A 200 mL undivided beaker cell (FIG. 1) was charged with 40 mL of $CCl_4$, 10 mL or $CH_3CN$ and 80 mL of saturated sodium chloride solution buffered at pH 7 with 0.25 M $Na_2HPO_4$. To this mixture was added $RuCl_3.3H_2O$ (20 mg, 0.08 mmol). Two platinum foil electrodes were immersed to the upper aqueous layer of the biphasic mixture. The mixture was electrolyzed at 24° C. under a constant current of 20 $MA/cm^2$ (applied voltage: 4.0 V) with moderate stirring. After the mixture turned yellow with $RuO_4$ when 5 F/mole of electricity had been passed based on the $RuCl_3$, L-diisopropyl tartrate cyclic sulfite (2.8 g, 10 mmol) dissolved in 5 mL of $CCl_4$ was added to the mixture. The solution turned to dark brown immediately and the electrolysis was continued at the same temperature and current until the solution turned to yellow (it required the passage of ca. 2.9 F/mole of electricity based on the tartrate cyclic sulfite). The electrodes were removed and the mixture was quenched with 2 mL of isopropyl alcohol to destroy the excess $RuO_4$. The black reduced ruthunium species was filtered off. The organic phase was separated and the aqueous phase was extracted with 2×30 mL of $CH_2Cl_2$. The combined organic phases were washed with saturated $NaHCO_3$ and brine, dried over $MgSO_4$. After removal of solvents in vacuo, L-diispropyl tartrate cyclic sulfate was obtained as a colorless oil (2.79 g. 94.3% yield). $[\alpha]^{25}D = -71.5$ (c 4.4, $CHCl_3$), $^1H$ NMR ($CDCl_3$) $\delta 5.4$ (s, 2 H), 5.2 (m, 2 H) 1.3–1.4 (d, 12 H). IR (film) 2980, 1740, 1460, 1410, 1280, 1210, 1140, 1100, 1060, 950, 850 $cm^{-1}$.

6.4. Example-2

L-Diisopropyl tartrate cyclic sulfite (0.46 g, 2 mmol) was oxidized at 21° C. using $RuCl_3.3H_2O$ (5 mg, 0.019 mmol) according to Example-1 in 20 mL of $CCl_4$ and 50 mL of saturated NaCl solution (buffered at pH 4.2 with 0.25 M sodium hydrogen phosphate) under constant current of 40 $mA/cm^2$. After the solution turned yellow from dark brown, the reaction was quenched with i-PrOH. L-Diisopropyl cyclic sulfate was obtained as a colorless oil after simple workup as Example-1 (0.42 g, 71% yield).

6.5. Example-3

L-Diethyl tartrate cyclic sulfite (0.63 g, 2.5 mmol) Was oxidized at 10°–23° C. using $Rucl_3.3H_2O$ (10 mg, 0.04 mmol) according to Example-1 in 30 mL or $CCl_4$ and 60 mL of saturated NaCl solution (buffered at pH 7) under constant current of 20 $mA/cm^2$. After passage of 6.3 F/mole of electricity, the reaction was quenched with i-PrOH. L-Diethyl tartrate cyclic sulfate was obtained as a white solid after simple workup as Example-1 (0.4 g, 61% yield). $^1H$ NMR ($CDCl_3$ $\delta 5.4$ (s, 2 H), 4.3 (q, J=8 Hz, 4 H), 1.3 (t, J=8 Hz, 6 H).

6.6. Example-4

1,2-Decanediol cyclic sulfite (1.1 g, 5 mmol) was oxidized at 25° C. using $RuCl_3.3H_2O$ (20 mg, 0.077 mmol) according to Example-1 in 30 mL of $CCl_4$ and 60 mL of saturated NaCl solution (buffered at pH 7) under constant current of 20 $mA/cm^2$. After passage of 2.5 F/mole of electricity, the reaction was quenched with i-PrOH. 1.2-Decanediol cyclic sulfate was obtained as a pale yellow oil after simple workup as Example-1 (1.16 g, 99% yield). $^1H$ NMR ($CDCl_3$ $\delta 4.92$–5.05 (m, $^1H$), 4.7 (dd, J=5.9, 8.6 Hz, 1 H), 4.34 (t, J=8.4 Hz, 1 H), 1.7–2.3 (m, 2 H), 1.2–1.5 (m, 12 H), 0.9 (t, J=6.5 Hz, 3 H). IR (film) 2931, 2861, 1469, 1391, 1216, 991, 829 $cm^{-1}$.

6.7. Example-5

3-Phenoxy-1,2-propanediol cyclic sulfite (1.1 g, 5 mmol) was oxidized using $RuCl_3.3H_2O$ (20 mg, 0.077 mmol) according to Example-1 in 20 mL of $CCl_4$, 10 mL of $CH_3CN$ and 60 mL of saturated NaCl solution (buffered at pH 7) under constant current of 20 $mA/cm^2$. After passage of 5.6 F/mole of electricity, the reaction was quenched with i-PrOH. 3-Phenoxy-1,2-propanediol cyclic sulfate was obtained as a colorless oil (solidified upon cooling) after simple workup as Example-1 (1.0 g, 87% yield). $^1H$ NMR ($CDCl_3$) $\delta 6.7$–7.4 (m, 5 H), 5.0–5.4 (m, 1 H), 4.6–4.8 (dd), J=3,5 Hz, 2 H), 4.2 (d,J=5 Hz, 2 H). IR (film) 2938, 1602, 1497, 1391, 1216, °991, 822 $cm^{-1}$.

6.8. Example-6

2,3-Butanediol cyclic sulfite (0.68 g. 5 mmol) was oxidized at 25° C. using $RuCl_3.3H_2O$ (20 mg, 0.077 mmol) according to Example-1 in 30 mL or CCl and 60 mL of saturated NaCl solution (buffered at pH 7) under constant current of 20 $mA/cm^2$. After passage of 2.5 F/mole of electricity, the reaction was quenched with i-PrOH. 2,3-Butanediol cyclic sulfate was obtained as a colorless oil after simple workup as Example-1 (0.70 g, 92% yield). $^1H$ NMR ($CDCl_3$) $\delta 4.5$–4.9 (m, 2 H), 1.5 (d, 6 H). IR (film) 2990, 2945, 1389, 1213, 1036, 923, 855 $cm^{31 1}$.

6.9. Example-7

2,3-Dimethyl-2,3-butanediol cyclic sulfite (pinacol sulfite) (8.02 g, 5 mmol) was oxidized at 20° C. using $RuCl_3.3H_2O$ (20 mg, 0.077 mmol) according to Example-1 in 20 mL of $CCl_4$, 10 mL of $CH_3CN$, and 60 mL of saturated NaCl solution (buffered at pH7) under constant current of 28 mA/cm$^2$. After message of 3.1 F/mole of electricity, the reaction was quenched with iPrOH. 2,3-Dimethyl 2,3-butanediol cyclic sulfate was obtained as a pale yellow solid after simple workup as Example-1 (0.80 g, 89% yield). $^1$H NMR (CDCl$_3$) δ1/6 (s. 12 H).

6.10. Example-8 cis-1,2-Cyclohexanediol cyclic sulfite (0.81 g, 5 mmol) was oxidized at 25° C. using $RuCl_3.3H_2O$ (20 mg, 0.077 mmol) according to Example-1 in 30 mL of $CCl_4$, 5 mL of $CH_3CN$ and 60 mL of saturated NaCl solution (buffered at pH 7) under constant current of 20 mA/cm$^2$. After passage of 4.1 F/mole of electricity, the reaction was quenched with i-PrOH. cis-1,2-Cyclohexanediol cyclic sulfate was obtained as a white solid after simple workup as Example-1 (0.70 g, 78.7% yield). $^1$H NMR (CDCl$_3$) δ4.8-5.2 (m, 2 H), 1.9-2.6 (m, 4 H), 1.3-2.0 (m, 4 H). IR (film) 2952, 1454, 1377, 1216, 815 cm$^{-1}$.

6.11. Example-9

1,2:5,6-Di-O-cyclohexylidene-D-mannitol cyclic sulfite (1.94 g, 5 mmol) was oxidized at 25° C. using $RuCl_3.3H_2O$ (20 mg, 0.077 mmol) according to Example-1 in 30 mL of $CCl_4$ and 60 mL of saturated NaCl solution (buffered at pH 7) under constant current of 20 mA/cm$^2$. After passage of 3.9 F/mole of electricity, the reaction was quenched with i-PrOH. 1,2:5,6-Di-O-cyclohexylidene-D-mannitol cyclic sulfate was obtained as a white solid after simple workup as Example-1 (1.84 g, 91% yield). $^1$H NMR (CDCl$_3$) δ4.0-4.9 (m, 8 H), 1.3-1.8 (bs, 20 H). IR (film) 1381, 1215, 1167 cm$^{-1}$.

6.12. Example-10

Ethylene sulfite (0.54 g, 5 mmol) was oxidized at 20° C. using $RuCl_3.3H_2O$ (20 mg, 0.077 mmol) according to Example-1 in 40 mL of $Ch_2Cl_2$ and 50 mL of saturated NaCl solution (buffered at pH 7) under constant current of 20 mA/cm$^2$. After passage of 5.5 F/mole of electricity, the reaction was quenched with i-PrOH. Ehtylene sulfate was obtained as a white solid after simple workup as Example-1 (0.01 g, 1.6% yield). $^1$H NmR (CDCl$_3$) δ4.7 (s, 4 H).

6.13. Example-11

1,3-Propanediol cyclic sulfite (0.61 g, 5 mmol) was oxidized at 27° C. using $RuCl_3.3H_2O$ (26 mg, 0.1 mmol) according to Example-1 in 35 mL of $CCL_4$ and 60 mL of saturated NaCl solution (buffered at pH 7) under constant current of 20 mA/cm$^2$. After passage of 5.3 F/mole of electricity, the reaction was quenched with i-PrOH. 1,3-Propanediol cyclic sulfate was obtained as a white solid after simple workup as Example-1 (0.28 g, 41% yield). $^1$H NMR (CDCl$_3$) δ4.8 (t, J=6 Hz, 4 H), 2.2 (dt, J=6 Hz, 2 H).

6.14. Example-12

2,4-Pentanediol cyclic sulfite (mixture of cis- and trans-isomers) (0.75 g, 5 mmol) was oxidized at 24° C. using $RuCl_3.3H_2O$) (20 mg, 0.077 mmol) according to Example-1 in 30 mL of $CCl_4$ and 60 mL of saturated NaCl solution (buffered at pH 7) under constant current of 20 mA/cm$^2$. After passage of 3.2 F/mole of electricity, the reaction was quenched with i-PrOH. 2,4-Pentanediol cyclic sulfate was obtained as a colorless oil after simple workup as Example-1 (0.71 g, 86% yield). $^1$H NMR (CDCl$_3$) δ4.7-5.3 (m, 2 H), 1.8-2.2 (m, 2 H), 1.6 (d, J=6 Hz, 6 H, for trans-isomer), 1.5 (d, J=6 Hz, 6 H, for cis-isomer). IR (film) 2995, 2952, 1391, 1209, 1082, 941, 878 cm$^{-1}$.

6.15. Example-13

L-Ephedrine cyclic sulfamidite (0.4 g, 1.9 mmol) was oxidized at 20° C. using $RuCl_3.3H_2O$ (20 mg, 0.077 mmol) according to Example-1 in 30 mL of $CH_2Cl_2$ and 60 mL of saturated NaCl solution (buffered at pH 8.5 with 0.25 M $Na_3PO_4$) under constant current of 20 m/cm$^2$. After passage of 4.5 F/mole of electricity, the reaction was quenched with i-PrOH. L-Ephedrine cyclic sulfamidate was obtained as a gray solid after simple workup as Example-1 (0.4 g, 93% yield, recrystallization from ether-$CH_2Cl_2$ gave a white solid, 0.3 g recovery). $^1$H NMR (CDCl$_3$) δ7.35 (s, 5 H), 5.6 (d, J=6.4 Hz, 1 H), 3.9 (dq, J=6.0, 6.4 Hz, 1 H), 2.75 (s, 3 H), 0.9 (d, J=6.0 Hz, 3 H), IR (film) 1460, 1335, 1286, 1210, 1162, 940, 836 cm$^{-1}$.

It should be apparent to one of ordinary skill that other embodiments can be readily contemplated which fall within the scope and spirit of the present invention. Thus, the present invention shall not be construed as limited to any of the specific embodiments described herein, but shall be limited only by the following set of claims.

What is claimed is:

1. A method of preparing a cyclic sulfate or sulfamidate compound of the formula (I) from the corresponding substrate of the formula (II),

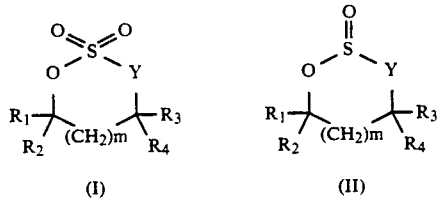

in which $R_1$, $R_2$, $R_3$ and $R_4$ may each, independently, be a hydrogen atom, a linear, branched or cyclic aliphatic alkyl group, which may optionally be substituted by one or more hetero atoms, a substituted or unsubstituted aromatic or heteroaromatic group, Y can be an oxygen or a group, N-$R_5$, in which $R_5$ is defined the same way as $R_1$-$R_4$ and m may be 0, 1 or 2, comprising:

(a) preparing an aqueous solvent medium that includes an effective amount of a metal species having a catalytically active state and an effective amount of a non-metal moiety that is capable of being oxidized electrochemically to an oxidant species;

(b) contacting said aqueous solvent medium with an organic solvent medium containing a substrate of the formula (II);

(c) applying a potential across a pair of electrodes that is in intimate contact with said aqueous solvent medium, such that said oxidant species is produced electrochemically and, through the action of said oxidant species, an amount of the catalytically active state of said metal species is maintained effective to mediate the production of the compound of the formula (I) from the oxidation of the substrate of the formula (II).

2. The method of claim 1 in which the group Y is oxygen.

3. The method of claim 1 in which the group Y is a group, N-R$_5$.

4. The method of claim 1 in which said metal is ruthenium.

5. The method of claim 1 in which said catalytically active state is ruthenium(VIII).

6. The method of claim 1 in which said non-metal moiety is a halide species.

7. The method of claim 6 in which said oxidant species is a chloride or hypochlorite ion.

8. The method of claim 1 in which said aqueous solvent medium comprises a saturated aqueous sodium chloride solution containing effective amounts of a ruthenium(IV) or ruthenium(III) species.

9. The method of claim 8 in which said oxidant is chloride cation.

10. The method of claim 9 in which said organic solvent medium comprises a halogenated hydrocarbon.

11. The method of claim 10 in which said organic solvent medium is water-immiscible and comprises carbon tetrachloride, methylene chloride or mixtures thereof.

12. The method of claim 11 in which said organic solvent medium further comprises acetonitrile.

13. The method of claim 5 in which said catalytically active state of ruthenium is RuO$_4$.

14. The method of claim 1 in which said compound of formula (I) is L-diisopropyltartrate cyclic sulfate and said compound of formula (II) is L-diisopropyltartrate cyclic sulfite.

15. The method of claim 1 in which said compound of formula (I) is 1,2-decanediol cyclic sulfate and said compound of formula (II) is 1,2-decanediol cyclic sulfite.

16. The method of claim 1 in which said compound of formula (I) is 3-phenoxy-1,2-propanediol cyclic sulfate and said compound of formula (II) is 3-phenoxy-1,2-propanediol cyclic sulfite.

17. The method of claim 1 in which said compound of formula (I) is cis-1,2-cyclohexanediol cyclic sulfate and said compound of formula (II) is cis-1,2-cyclohexanediol cyclic sulfite.

18. The method of claim 1 in which said compound of formula (I) is 1,2:5,6-di-O-cyclohexylidene-D-mannitol cyclic sulfate and said compound of formula (II) is 1,2:5,6-di-O-cyclohexylidene-D-mannitol cyclic sulfite.

19. The method of claim 1 in which said compound of formula (I) is L-ephedrine cyclic sulfamidate and said compound of formula (II) is L-ephedrine cyclic sulfamidite.

20. A method of preparing a cyclic sulfate or sulfamidate compound of the formula (I) from the corresponding substrate of the formula (II),

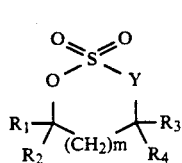  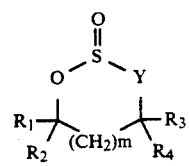

(I)  (II)

in which R$_1$, R$_2$, R$_3$ and R$_4$ may each be, independently, a hydrogen atom, a linear, branched or cyclic aliphatic alkyl group, which may be optionally substituted by one or more hetero atoms, a substituted or unsubstituted aromatic or heteroaromatic group, Y can be an oxygen or a group, N-R$_5$, in which R$_5$ is defined the same way as R$_1$-R$_4$ and m may be 0, 1 or 2, comprising:

(a) preparing an aqueous solvent medium comprising a buffered saturated aqueous sodium chloride solution that includes an effective amount of a ruthenium species that is capable of being converted to a catalytically active ruthenium(VIII) species;

(b) contacting said aqueous solvent medium with an organic solvent medium comprising a halogenated hydrocarbon solvent in which a substrate of the formula (II) is dissolved;

(c) applying a potential across a pair of electrodes that is in intimate contact with said aqueous solvent medium, such that chloride-derived oxidant species is produced electrochemically and, through the action of said chloride-derived oxidant species, an amount of the catalytically active ruthenium(VIII) species is maintained which is effective to mediate the production of the compound of the formula (I) from the oxidation of the substrate of the formula (II).

* * * * *